United States Patent
Karol et al.

(10) Patent No.: US 7,041,825 B2
(45) Date of Patent: *May 9, 2006

(54) ADDITIVE COMPOUND FOR CURING HALOGENATED POLYMERS

(75) Inventors: Thomas J. Karol, Holualoa, HI (US); Francis S. Cheng, West Hartford, CT (US); Ronald J. Tepper, Fairfield, CT (US)

(73) Assignee: R.T. Vanderbilt Company, Inc., Norwalk, CT (US)

( * ) Notice: Subject to any disclaimer, the term of this patent is extended or adjusted under 35 U.S.C. 154(b) by 161 days.

This patent is subject to a terminal disclaimer.

(21) Appl. No.: 10/776,957

(22) Filed: Feb. 11, 2004

(65) Prior Publication Data

US 2004/0176504 A1    Sep. 9, 2004

Related U.S. Application Data

(60) Continuation-in-part of application No. 10/618,461, filed on Jul. 11, 2003, now abandoned, which is a division of application No. 09/726,344, filed on Dec. 1, 2000, now Pat. No. 6,635,696.

(51) Int. Cl.
*C07D 403/00*     (2006.01)

(52) U.S. Cl. .................... 544/359; 508/274; 548/148; 524/84; 525/373

(58) Field of Classification Search ............... 544/359; 508/274; 548/148; 524/84; 525/373
See application file for complete search history.

(56) References Cited

U.S. PATENT DOCUMENTS

| 3,940,408 | A | 2/1976 | Waldbillig | 260/306.8 |
|---|---|---|---|---|
| 4,128,510 | A | 12/1978 | Richwine | 528/36 |
| 4,358,597 | A | 11/1982 | Fields | 584/142 |
| 5,391,621 | A | 2/1995 | Ohm et al. | 525/160 |
| 5,538,652 | A | 7/1996 | Farng et al. | 508/231 |
| 5,686,397 | A | 11/1997 | Baranski et al. | 508/274 |
| 5,773,523 | A | 6/1998 | Karol et al. | 525/330.4 |
| 6,255,259 | B1 * | 7/2001 | Camenzind et al. | 508/271 |

* cited by examiner

*Primary Examiner*—Peter D. Mulcahy
(74) *Attorney, Agent, or Firm*—Norris McLaughlin & Marcus PA

(57) ABSTRACT

The present invention relates to 1,3,4-thiadiazole reaction products useful as accelerators and/or curing agents for halogenated polymers in rubber vulcanization processes, and to halogenated polymer compositions containing the thiadiazole derivatives, as well as a method of preparing the same.

The additive is the reaction product of a 1,3,4-thiadiazole compound and a dithiocarbamic acid or an amine, or an isomer thereof.

36 Claims, No Drawings

ADDITIVE COMPOUND FOR CURING HALOGENATED POLYMERS

This is a continuation-in-part of U.S. Ser. No. 10/618,461, filed Jul. 11, 2003 now abandoned which is a divisional of U.S. Ser. No. 09/726,344, filed Dec. 1, 2000, now U.S. Pat. No. 6,635,696.

BACKGROUND OF INVENTION

The present invention relates to 1,3,4-thiadiazole reaction products useful as accelerators and/or curing agents for halogenated polymers in rubber vulcanization processes, and to halogenated polymer compositions containing the thiadiazole derivatives, as well as a method of preparing the same.

Vulcanizable rubber compositions present certain inherent problems in terms of handling and storage. For example, prior to the curing, the uncured rubber may often degrade during storage due to hydrolytic instability of the additives contained therein. As a result the cure reproducibility from batch to batch in the vulcanization process can often vary. However, batch-to-batch cure reproducibility is an important parameter of quality control.

It is known that halogen-containing polymers may be compounded with curing agents, accelerators and other compounds in order to prepare vulcanizable rubber compositions which are useful in a variety of applications. A description of curing agents and accelerators, as well as other components of natural and synthetic rubbers can be found in Kirk-Othmer's Encyclopedia of Chemical Technology, John Wiley & Sons, 4th Edition, at pages 460–481.

Despite the availability of curing agents and/or accelerators for halogenated polymers, there is a continuing need for curing agents and/or accelerators that allow for good bin storage characteristics and improved batch-to-batch cure reproducibility.

Accordingly, it is an object of the present invention to compounds useful as curing agents and/or accelerators for rubber vulcanization processes which provide good bin storage properties for uncured rubber and improved consistency in cure reproducibility.

It is yet another object of the present invention to provide curable rubber compositions which exhibit good bin storage properties and improved consistency in cure reproducibility and methods of preparing the cured rubber compositions.

SUMMARY OF THE INVENTION

In accordance with the present invention, an additive is provided which represents the reaction product of a 1,3,4-thiadiazole compound and a dithiocarbamic acid or an amine, or an isomer thereof.

The present invention also provides a curable polymer composition including at least one halogenated polymer and the above-described additive of the present invention. A method is also provided for preparing a cured polymer composition including at least one halogenated polymer and the additive of the invention. The additives of the present invention are particularly useful as curing agents and/or accelerators for halogen-containing polymer compositions, and provide good bin storage characteristics for the uncured polymer composition and improved cure reproducibility. These and other advantages of the present invention will be more readily apparent from the detailed description set forth below.

DETAILED DESCRIPTION OF THE INVENTION

It has now been discovered that a reaction product of a 1,3,4-thiadiazole compound and either a dithiocarbamic acid or an amine, or an isomer thereof, are useful additives, particularly as curing agents and accelerators in halogen-containing polymer compositions. The thiadiazole derivatives of the present invention have been found to provide good bin storage characteristics and improved cure reproducibility when used as additives in halogen-containing polymer compositions.

The 1,3,4-thiadiazole reaction products of the invention can be readily produced as reaction products following the method steps described herein.

In one embodiment of the invention, a 1,3,4-thiadiazole compound represented by formula (I)

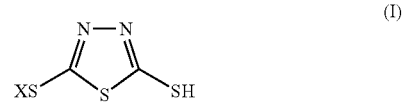

wherein X is hydrogen or a $C_1$–$C_{20}$ alkyl group; is reacted with either a dithiocarbamic acid represented by formula (IIa), or an amine by formula (IIb)

wherein $R_1$ and $R_2$ are independently a radical selected from the group consisting of hydrogen, an alkyl, a cycloalkyl, an alkenyl, an aryl, an arylalkyl, and an alkylaryl, or $R_1$ and $R_2$ together form 3- to 8-membered heterocyclic ring structure which optionally contains an additional nitrogen or an oxygen heteroatom and wherein the heterocyclic ring is optionally substituted with alkyl groups wherein the total number of carbon atoms from the heterocyclic ring alkyl groups is from 4 to 40. As known in the art, dithiocarbamic acid is not readily isolatable and thus, in one embodiment of the invention, needs to be formed in situ to provide the starting material. The dithiocarbamic acid of formula (IIa) is synthesized in situ by reacting carbon disulfide with the appropriate secondary amine. The reaction is carried out, and the oxidizing agent is then added. The reaction may also be carried out by adding the 1,3,4-thiadiazole derivative (I) directly to the amine (IIb), and then adding the oxidizing agent. The reaction conditions (e.g., temperature and time) are variable and can be easily modified by one of ordinary skill in the art following the teachings set forth herein. In another embodiment of the invention, $R_1$ and $R_2$ are independently a radical selected from the group consisting of hydrogen, a $C_1$–$C_8$-alkyl, a $C_3$–$C_8$-cycloalkyl, a $C_1$–$C_8$-alkenyl, an aryl, an aryl-$C_1$–$C_8$-alkyl, or a $C_1$–$C_8$-alkylaryl.

In another embodiment of the invention, a thiadiazole reaction product of the invention can be synthesized by reacting a compound of formula (I) where X is hydrogen, with the monoamino dithiocarbamic acid of formula (IIa) or the amine of formula (IIb) in which $R_1$ and $R_2$ are independently a hydrogen, an alkyl, a cycloalkyl, an alkenyl, an aryl, an arylalkyl, and an alkylaryl, or $R_1$ and $R_2$ together form 3- to 8-membered heterocyclic ring structure which optionally contains an additional nitrogen or an oxygen heteroatom and wherein the heterocyclic ring is optionally substituted with alkyl groups wherein the total number of carbon atoms from the heterocyclic ring alkyl groups is from 4 to 40, wherein when an amine of formula (IIb) is used, the compound of formula (I) is added to the amine of formula (IIb) with subsequent addition of an oxidizing agent.

In another embodiment of the invention, $R_1$ and $R_2$ are independently a radical selected from the group consisting of hydrogen, a $C_1$–$C_8$-alkyl, a $C_3$–$C_8$-cycloalkyl, a $C_1$–$C_8$-alkenyl, an aryl, an aryl-$C_1$–$C_8$-alkyl, or a $C_1$–$C_8$-alkylaryl.

In another embodiment of the invention, $R_1$ and $R_2$ are the same and are a radical selected from the group consisting of hydrogen, a $C_1$–$C_8$-alkyl, a $C_3$–$C_8$-cycloalkyl, a $C_1$–$C_8$-alkenyl, an aryl, an aryl-$C_1$–$C_8$-alkyl, or a $C_1$–$C_8$-alkylaryl.

In another embodiment of the invention, $R_1$ and $R_2$ are the same and are selected from the group consisting of ethyl, isopropyl and butyl and the dithiocarbamic acid is synthesized in situ by reacting carbon disulfide with the corresponding dialkylamine and where the reaction is carried out in the presence of an oxidizing agent.

In another embodiment of the invention, $R_1$ and $R_2$ of formula (IIa) or formula (IIb) together form 3- to 8-membered heterocyclic ring structure which optionally contains an additional nitrogen or an oxygen heteroatom and wherein the heterocyclic ring is optionally substituted with alkyl groups wherein the total number of carbon atoms from the heterocyclic ring alkyl groups is from 4 to 40.

In another embodiment of the invention, $R_1$ and $R_2$ of the dithiocarbamic acid of formula (IIa) together form 5- to 8-membered heterocyclic ring structure which optionally contains an additional nitrogen heteroatom.

In another embodiment of the invention, $R_1$ and $R_2$ of the dithiocarbamic acid of formula (IIa) form a 6-membered heterocyclic ring with one additional nitrogen heteroatom (e.g. 1,4-piperazine dithiocarbamic acid), which can be synthesized by first forming in situ bis-(1,4-piperazine dithiocarbamic acid) from homopiperazine and carbon disulfide. This diamino dithiocarbamic acid thus formed is then reacted with a 2,5-dimercapto-1,3,4-thiadiazole in the presence of an oxidizing agent.

In another embodiment of the invention, the reaction is carried out in the presence of an oxidizing agent.

In another embodiment of the invention, the oxidizing agent is selected from the group consisting of sodium hypochlorite, chlorine, oxygen, dichromates, chlorochromates, manganese dioxide, ferric chloride, diethyl azodicarboxylate, calcium hypochlorite, thallium acetate, dimethylsulfoxide/iodine, sodium perborate, nitric oxide, nitrogen dioxide and hydrogen peroxide.

In another embodiment of the invention, the reaction is carried out in the presence of hydrogen peroxide as the oxidizing agent.

While not wishing to be limited by theory, it is believed that when a monoamino dithiocarbamic acid is used in the reaction, the reaction products include compounds with the following structures:

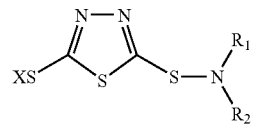

Where X is hydrogen, it is believed that the following additional structures are possible which are represented below:

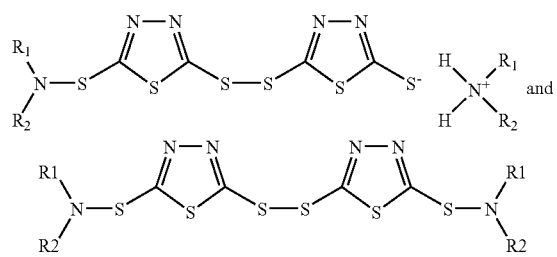

The reaction mixture may also contain the mono amine salt of the thiadiazole derivative, shown below.

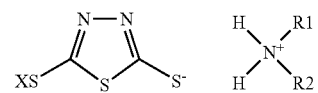

The compounds contained in the product may vary depending on the amount of hydrogen peroxide used in the reaction.

Likewise, it is believed that when a diamino dithiocarbamic acid is used in the reaction, the reaction products include compounds with the following structures (1,4 piperazine is used as a representative example for use of diamino dithiocarbamic acids):

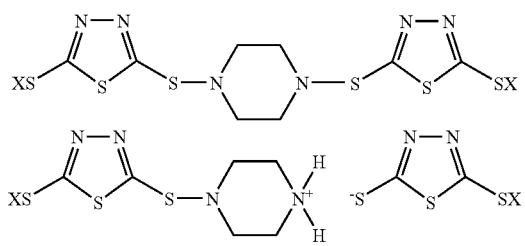

Where X is hydrogen, it is believed that the following additional structures are possible which are represented below:

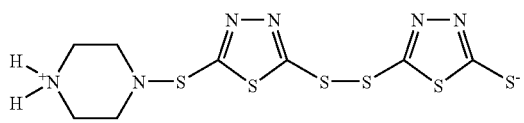

-continued

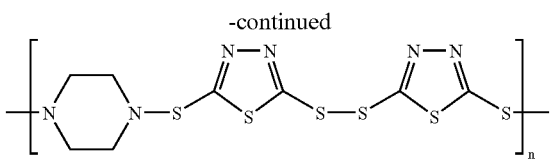

The reaction may also contain the amine salt of the thiadiazole derivative, shown below.

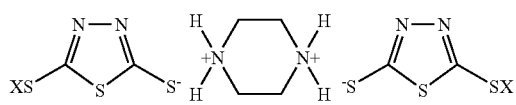

Those skilled in the art will recognize that the additives, i.e. the reaction products, of the invention may additionally contain positional isomers of the derivatives which are reaction products formed according to the above methods, due to tautomerization or other similar rearrangement of the substituents on the DMTD moiety. In accordance with the invention, reference to "an isomer thereof" means positional isomers. Positional isomers of the derivatives of the invention are also useful as curing agents and accelerators.

The above-described additives of the invention, alone or in combination, are admixed with a major amount of at least one halogenated polymer to provide a curable (i.e., vulcanizable) polymer composition. The polymer composition is then cured following conventional techniques known in the art to produce a cured (i.e., vulcanized) polymer composition.

In accordance with the present invention, any saturated or unsaturated halogen-containing (i.e., halogenated) polymer may be used. Preferably, the polymer contains at least one percent by weight halogen with about five percent being more preferred. The halogen content in the polymer may range up to 40 percent based on the weight of the polymer. Preferably, the halogen-containing polymers is an elastomer. In another preferred embodiment, the halogen-containing polymer is a chlorine-containing (i.e., chlorinated) polymer. Representative examples of chlorine-containing polymers to be used in accordance with the present invention include, but are not limited to, homopolymers of epichlorohydrin, copolymers of epichlorohydrin and ethylene oxide or propylene oxide, polychloroprene, chlorinated polyolefins, chlorosulfonated polyolefin, polychloroalkylacrylates and chlorobutyl rubber. These polymers are well known in the art and are available commercially from variety of sources. One particularly preferred chlorinated polymer is chlorinated polyethylene "CPE" which is commercially available from DuPont Dow under the tradename Tyrin©.

The halogen-containing polymers may be blended with non-halogen containing polymers as along as a sufficient halogen content is provided in the polymer composition to effect crosslinking. The blends can include, but are not limited to, natural rubber, polybutadiene, polyolefins, copolymers of butadiene with styrene (SBR) or acrylonitrile (NBR), copolymers of ethylene-propylene-diene (EPDM), butyl rubber and the like. Such blends may contain from about 10 to about 90% by weight of each type of polymer. In a more preferred embodiment, the blends contain the halogenated polymer at levels from about 25 to 75% by weight with respect to the total weight of the polymer blend.

The additives of the invention may be incorporated into the polymer composition in their pure form or they may be mixed with one or more liquid diluents. They also may be adsorbed onto the surface of a finely divided, inert carrier to provide a powdered product. When the additives of the invention are mixed with a liquid diluent or finely divided carrier, the additive may range from 15 to 85 percent by weight of the composition with the remainder being the diluent, carrier or a combination thereof. Preferably, the additives of the invention are mixed in a ratio ranging from 30 to 70 percent by weight.

The suitable diluents, among others, include aromatic, naphthenic and paraffinic hydrocarbon oil, polyglycols and glycols, alkyl esters of dibasic acids, e.g., dioctyl phthalate, dioctyl sebacate, dioctyl adipate, diisodecyl glutarate, dioctyl azolate, alkyl sulfides, fatty acid esters, e.g., butyl oleate, butyl stearate, octyl epoxy tallate, trioctyl trimellitate, polyester plasticizers, e.g., polymeric di(butoxyethoxy-ethyl) adipate, polymers of bis(ethyleneoxy)methane with disulfide linkages; petroleum sulfonates, alkyl trimellitates; and polymeric esters.

The suitable finely divided carrier materials include carbon black, metal oxides, such as aluminum oxide, alumina, silica, mineral fillers, such as clay, talc and betonite, aluminosilicate, zeolites, calcium silicate and similar carriers. Preferred carriers have a surface area of from about 75 to about 300 m2/gm. A particularly preferred carrier is amorphous silica available from Pittsburgh Plate Glass Company under the tradename HISIL®233 and HISIL® ABS.

The amount of the additive effective to cure the chlorinated polymer will vary as a function of the halogen content in the halogenated polymer. Generally, the additives are employed in the range from about 0.1 to about 10.0 parts by weight per 100 parts by weight of halogenated polymer present in the curable composition. More preferably, the additives of the present invention are present in the amount from about 0.5 to about 5.0 parts by weight per 100 parts by weight of the halogenated polymer. If a diluent or a carrier material is added to the curable polymer composition, higher levels of the additive may be required.

Additional accelerators of the aliphatic or aromatic amine type can also be used if the halogenated polymer employed for production of vulcanized rubber is relatively unreactive. The suitable accelerators, among others, include the reaction product of butyraldehyde and aniline (available commercially under the tradename VANAX© RTM 808 from R.T. Vanderbilt Company, Inc.), fatty amines, sulfenamides such as N-cyclohexyl-2-benzothiazolesulfenamide (available commercially under the tradename DURAX® from R.T. Vanderbilt Company, Inc.) and quaternary ammonium salts, such as tetrabutylammonium bromide and tetraethylammonium chloride. A listing of additional accelerators to be utilized in accordance with the present invention is set forth in "Rubber Chemicals," J. Van Alphen, pages 1–46 (1973), which is incorporated herein by reference.

For curing blends of halogenated and non-halogenated polymers, sulfur or other well known sulfur-containing curatives for unsaturated elastomers may be included in the composition. Examples of such compounds include, but are not limited to, sulfur, benzothiazyl disulfide, N-oxydiethylene benzothiazole-2-sulfonamide, 2-mercaptobenzo-thiazole, alkyl phenol disulfides, tetraalkylthiuram disulfide and monosulfide having normal or branched chain alkyl groups, m-phenylene-bismaleimide and N,N'-diarylguanidines.

Other additives, which may be desirable to effect crosslinking along with the derivatives of the present invention, include basic metal oxides, metal hydroxides and metal salts of carboxylic acids. The typical additives include zinc oxide, magnesium oxide, zinc stearate and sodium acetate. The magnesium oxide may be synthetic or a natural magnesite mineral. The magnesite may be calcined or treated by other similar processes to yield a predominantly magnesium oxide product.

In addition to the curatives, the polymer compositions of the invention may also include antioxidants, for example, octylated diphenylamine, diphenyl-p-phenylenediamine and styrenated phenol type antioxidants. Likewise, the polymer compositions of the invention may include antidegradants, antiozonants, antiflexcracking agents, heat stabilizers and metal poison-inhibitors, which are well known in the art.

The curable compositions may be prepared and blended using any suitable mixing device such as a two-roll mill, an internal mixer (Brabender Plasticorder), a Banbury Mixer, a kneader or a similar mixing device. The processing and vulcanization techniques are well known in the art.

The following non-limiting examples are given to further illustrate the additives of the invention and their use in curable polymer compositions. All percentages and parts are based on weight unless otherwise indicated.

EXAMPLE 1

A 1,3,4-thiadiazole reaction product was prepared in the following manner. In 100 grams of isopropyl alcohol, 20.5 grams of diisopropylamine was combined with 16 grams of carbon disulfide (CS2) and held at a temperature of about 27° C. for about 1 hour. Subsequently, 30 g of a 2,5-dimercapto-1,3,4-thiadiazole was added to the mixture and then 20 g of 35 wt. % hydrogen peroxide. The mixture was reacted for about 1 hour at a temperature of about 28° C. to yield a solid end product. The isopropyl alcohol was removed by filtration and saved for recovery.

EXAMPLE 2

A 1,3,4-thiadiazole reaction product was prepared in the following manner. In 100 grams of isopropyl alcohol 26 grams of dibutyl amine was combined with 16 grams of CS2 and held at a temperature of about 40° C. for about 1 hour. Subsequently, 30 grams of 2,5-dimercapto-1,3,4-thiadiazole was added to the mixture and then 20 grams of 35 wt. % hydrogen peroxide were added. The mixture was reacted for about 1 hour at a temperature of about 28° C. to yield a liquid end product.

EXAMPLE 3

A 1,3,4-thiadiazole reaction product was prepared in the following manner. In 100 grams of isopropyl alcohol 17 grams of piperidine was combined with 16 grams of $CS_2$ and held at a temperature of about 35° C. for about 1 hour. Subsequently, 30 grams of 2,5-dimercapto-1,3,4-thiadiazole was added to the mixture along and then 20 grams of 35 wt. % hydrogen peroxide were added. The mixture was reacted for about 1 hour at a temperature of about 35° C. to yield a solid end product. The isopropyl alcohol was removed by filtration and saved for recovery.

EXAMPLE 4

A 1,3,4-thiadiazole reaction product was prepared in the following manner. In 100 grams of isopropyl alcohol 15 grams of diethylamine was combined with 16 grams of carbon disulfide ($CS_2$) and held at a temperature of about 27° C. for about 1 hour. Subsequently, 30 g of a 2,5-dimercapto-1,3,4-thiadiazole was added to the mixture and then 20 g of 35 wt. % hydrogen peroxide were added. The mixture was reacted for about 1 hour at a temperature of about 28° C. to yield a solid end product. The isopropyl alcohol was removed by filtration and saved for recovery.

EXAMPLE 5

A 1,3,4-thiadiazole reaction product was prepared in the following manner. To a reaction flask was added 782.3 grams of di-n-buytlamine, 1530.8 grams of water and 937.6 grams of 2,5-dimercapto-1,3,4-thiadiazole. Then 588.3 grams of 35% hydrogen peroxide was added over a period of five and one half hours. After the hydrogen peroxide had completely reacted, the reaction was heated to 116° C., and placed under vacuum to remove all of the water, giving a viscous product. The product (259.3 grams) was then distributed on Microcel E (111.2 grams) to give a 70% active solid.

EXAMPLE 6

A 1,3,4-thiadiazole reaction product was prepared in the following manner. To a reaction flask was added 1700 grams of isopropanol, and 116 grams of piperazine. This was mixed for 30 minutes until the piperazine had completely dissolved. Then 700 grams of water and 400 grams of 2,5-dimercapto-1,3,4-thiadiazole was added, and the mixture was mixed for 45 minutes. The reaction mixture was cooled to 10° C. in an ice bath, and 259 grams of 35% hydrogen peroxide was added. The temperature was kept below 42° C. during the addition of the hydrogen peroxide. After the addition, the reaction mixture was mixed for one hour, and then heated to 80–90° C. and stirred for three hours. The reaction mixture was then cooled to room temperature, and the solid product was collected by filtration.

EXAMPLE 7

A 1,3,4-thiadiazole reaction product was prepared in the following manner. To a reaction flask was added 109.8 grams of di-n-butylamine, 538.4 grams of water, and 131.8 grams of 2,5-dimercapto-1,3,4-thiadiazole. This mixture was then heated to 60° C., and after thirty minutes was allowed to cool back to 41° C. Then 20.5 grams of 35% hydrogen peroxide was added over a period of ten minutes. After the hydrogen peroxide had completely reacted, the organic layer was transferred to a round bottom flask, and the excess water was removed with a rotary evaporator, giving a viscous liquid. 95.5 grams of the product was then distributed on 40.9 grams of Microcel E to give a 70% active solid.

EXAMPLE 8

A 1,3,4-thiadiazole reaction product was prepared in the following manner. To a reaction flask was added 96.6 grams of di-n-butylamine, 76.0 grams of water, and 115.7 grams of 2,5-dimercapto-1,3,4-thiadiazole. The mixture was then heated to 55° C., and then allowed to cool back to 36° C. Then 36.2 grams of 35% hydrogen peroxide was added over a period of one and one half hours. After the peroxide was added, 10 milliliters of additional water was added. The reaction was then heated to 118° C. under vacuum to remove the excess water. The product (172.0 grams) was then distributed on Microcel E (73.6 grams) giving a 70% active solid.

EXAMPLE 9

A 1,3,4-thiadiazole reaction product was prepared in the following manner. To a reaction flask was added 62.7 grams of di-n-butylamine, 114.8 grams of water, and 74.9 grams of 2,5-dimercapto-1,3,4-thiadiazole. Then 70.8 grams of 35% hydrogen peroxide was added over a period of one hour and forty five minutes. An additional 10 mL of water was added, and the mixture was stirred for an additional two hours at room temperature. The reaction mixture was then heated to 111° C., and the water was removed by distillation. Then 111.4 grams of the product was distributed on 47.6 grams of Microcel E giving a 70% active solid product.

EXAMPLE 10

Vulcanizates incorporating the derivatives of Examples 1–4 were prepared and evaluated. Samples were prepared by compounding chloropolyethylene polymer with the derivatives of Examples 1–4 (neat) and various other additives as listed in Table 1 below.

TABLE 1

| | Sample | | | | | | |
|---|---|---|---|---|---|---|---|
| | 1 | 2 | 3 | 4 | 5 | 6 | 7 |
| Components (parts by weight) | | | | | | | |
| Chloropolyethylene (1) | 100 | 100 | 100 | 100 | 100 | 100 | 100 |
| Carbon Black (2) | 50 | 50 | 50 | 50 | 50 | 50 | 50 |
| Magnesium Oxide (3) | 5 | 5 | 5 | 5 | 5 | 5 | 5 |
| Process oil (4) | 30 | 30 | 30 | 30 | 30 | 30 | 30 |
| Amine Activator (5) | 0.8 | 0.8 | 0.8 | 0.8 | 0.8 | — | — |
| Retarding Agent (6) | | | | | 0.5 | | |
| Inventive Curative | | | | | | | |
| Example 1 | 2.5 | | | | | 2.5 | |
| Example 2 | | 2.5 | | | 2.5 | | |
| Example 3 | | | 2.5 | | | | |
| Example 4 | | | | 2.5 | | | 2.5 |
| Total Parts: | 188.3 | 188.3 | 188.3 | 188.3 | 188.8 | 187.5 | 187.5 |

(1) Commercially available from DuPont Dow Elastomer as Tyrin CM0136.
(2) Commercially available from Degussa Chemical as N774.
(3) Commercially available from Marine Magnesium Company as Maglite* D.
(4) Commercially available from Sun Oil and Refining Company as Sundex' 790
(5) Commercially available from R.T. Vanderbilt Company, Inc., as Vanax' '882B.
(6) N-(cyclohexylthio)phthalimide - commercially available from R.T. Vanderbilt Company, Inc., as Vantard" PVI.

The compositions were pressed cured at 171° C. for 30 minutes. The samples were evaluated for Torque and Scorch time by ASTM D2084. The Torque and Scorch results for the samples are listed in Table 2 below.

TABLE 2

| | Sample | | | | | | |
|---|---|---|---|---|---|---|---|
| | 1 | 2 | 3 | 4 | 5 | 6 | 7 |
| Oscillating Disk Rheometer 60 minutes @ 171° C. | | | | | | | |
| Minimum Torque (ML) (inch-pounds) | 2.6 | 2.9 | 2.0 | 2.6 | 2.9 | 3.2 | 3.5 |
| Maximum Torque (MH) (inch-pounds) | 46.4 | 49.2 | 43.9 | 53.9 | 45.6 | 44.3 | 49.4 |
| Scorch time, (ts2) (minutes) | 1.0 | 1.4 | 2.9 | 1.7 | 1.6 | 1.2 | 1.3 |
| Cure time, (tc90) (minutes) | 15.5 | 11.5 | 27.5 | 22.5 | 10.5 | 19.0 | 24.0 |

EXAMPLE 10, CONTINUED

Vulcanizates incorporating the derivatives of Examples 5–9 were prepared and evaluated. Samples were prepared by compounding chloropolyethylene polymer with the derivatives of Examples 5–9 a and various other additives as listed in Table 3 below.

TABLE 3

| | Sample | | | | |
|---|---|---|---|---|---|
| | 8 | 9 | 10 | 11 | 12 |
| Components (parts by weight). | | | | | |
| Chloropolyethylene (1) | 100 | 100 | 100 | 100 | 100 |
| Carbon Black (2) | 50 | 50 | 50 | 50 | 50 |
| Magnesium Oxide (3) | 5 | 5 | 5 | 5 | 5 |
| Process oil (4) | 30 | 30 | 30 | 30 | 30 |
| Inventive Curative: | | | | | |
| Example 5 | 5.0 | | | | |
| Example 6 | | 2.5 | | | |
| Example 7 | | | 5.0 | | |
| Example 8 | | | | 5.0 | |
| Example 9 | | | | | 5.0 |
| Total Parts: | 190.0 | 187.5 | 190.0 | 190.0 | 190.0 |

(1) Commercially available from DuPont Dow Elastomer as Tyrin CM0136.
(2) Commercially available from Degussa Chemical as N774.
(3) Commercially available from Marine Magnesium Company as Maglite D.
(4) Commercially available from Sun Oil and Refining Company as Sundex 790

The cure properties were evaluated by test method ASTM D5289. The results are shown below. Physical properties (Stress Strain Tests, ASTM D412 Method A and Hardness, ASTM D2240) are also shown below.

TABLE 4

ASTM D5289, Moving Die Rheometer at 169.4° C. (340.5° F.), 0.5° Arc

| | Sample | | | | |
|---|---|---|---|---|---|
| | 8 | 9 | 10 | 11 | 12 |
| Minimum Torque, ML, dN-m | 1.05 | 0.54 | 1.19 | 1.05 | 1.07 |
| Minimum Torque, ML, lbf-in | 0.93 | 0.48 | 1.05 | 0.93 | 0.95 |
| Maximum Torque, MH, dN-m | 17.23 | 13.76 | 20.07 | 18.97 | 15.12 |
| Maximum Torque, MH, lbf-in | 15.25 | 12.18 | 17.76 | 16.79 | 13.38 |
| Ts2, minutes | 0.96 | 6.38 | 0.97 | 1.05 | 0.94 |
| T'90, minutes | 6.48 | 29.25 | 6.03 | 6.17 | 11.07 |
| Cure Rate Index, min-1 | 18.12 | 4.37 | 19.8 | 19.53 | 9.87 |

TABLE 4-continued

ASTM D5289, Moving Die Rheometer at 169.4° C. (340.5° F.), 0.5° Arc

| | Sample | | | | |
|---|---|---|---|---|---|
| | 8 | 9 | 10 | 11 | 12 |
| Cure Rate, dN-m/min. | 2.93 | 0.58 | 3.73 | 3.50 | 1.39 |
| Cure Rate, lbf-in/min. | 2.59 | 0.51 | 3.30 | 3.10 | 1.23 |
| Tan Delta at ML | 1.08 | 1.62 | 0.98 | 1.08 | 1.06 |
| Tan Delta at MH | 0.06 | 0.10 | 0.04 | 0.05 | 0.08 |
| ASTM D412, Method A - Stress, Strain Tests at 21° C. (70° F.) | | | | | |
| 100% Modulus, MPa | 4.53 | | 5.05 | 5.15 | 4.14 |
| Tensile Strength, MPa | 20.72 | | 21.63 | 20.43 | 19.73 |
| Elongation at Break, % | 448 | | 399 | 414 | 508 |
| ASTM D2240 - Shore A Durometer at 21° C. (70° F.) | | | | | |
| Points | 71.3 | | 71.4 | 70.0 | 69.2 |

EXAMPLE 11

A comparative study was conducted to evaluate bin-storage stability of vulcanizable composition compounded with the derivative produced in accordance with Example 2 and the curative "Echo A" which is commercially available from Hercules, Inc. Echo A, CAS. No. 51988-14-8, is known in the art as 2,5-dimercapto-1,3,4-thiadiazole monobenzoate ester which corresponds to the structure:

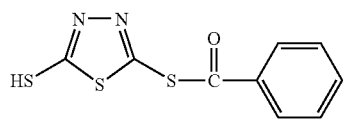

Samples were prepared by compounding the components listed in Table 5. Differing amounts of Echo A and the Example 2 derivative were utilized to provide an equimolar ratio of thiadiazole moiety due to differing molecular weights of the curatives. Likewise, differing amounts of the accelerators Vanax® 808 Liquid and Durax® were also utilized to provide an equimolar ratio of accelerator.

TABLE 5

| | Samples | | | | |
|---|---|---|---|---|---|
| | 13 | 14 | 15 | 16 | 17 |
| Components (parts by weight) | | | | | |
| Tyrin ® CPE0136 | 100 | 100 | 100 | 100 | 100 |
| N650(¹) | 40 | 40 | 40 | 40 | 40 |
| Atomite ® Whiting(2) | 75 | 75 | 75 | 75 | 75 |
| Dioctyl phthalate (DOP) | 15 | 15 | 15 | 15 | 15 |
| Sundex © 790 | 20 | 20 | 20 | 20 | 20 |
| Elastomag ® 170(3) | 7.5 | 10 | 5 | 5 | 10 |
| Carbowax ® 3350(4) | 1 | 1 | 1 | 1 | 1 |
| PE617A(5) | 2 | 2 | 2 | 2 | 2 |
| Example 2 | — | 5.02 | 5.02 | 5.02 | 5.02 |
| Echo A | 2.5 | — | — | — | — |
| Vanax° 808 Liquid (6) | 0.8 | — | — | — | — |
| Durax © (⁷) | — | 1.5 | 1.5 | 0.5 | 0.5 |
| Total Parts: | 263.8 | 269.5 | 264.5 | 263.5 | 268.5 |

(1) Carbon Black commercially available from Degussa Chemical.
(2) Calcium carbonate commercially available from Thompson & Weinman.
(3) Magnesium oxide commercially available from Elastochem.
(4) Polyethylene glycol commercially available from Union Carbide.
(5) Low molecular weight polyethylene commercially available from Allied Signal, Inc.
(6) Accelerator (butrylaldehyde-amine condensation adduct) commercially available from R.T. Vanderbilt Company, Inc.
(7) Accelerator (N-cyclohexyl-2-benzothiazolesulfenamide) commercially available from R.T. Vanderbilt Company, Inc.

Samples were evaluated for Mooney Parameters using a small rotor (MS), Torque and Scorch times, and Physical properties, with the results being listed Table 6.

TABLE 6

| | Sample | | | | |
|---|---|---|---|---|---|
| | 13 | 14 | 15 | 16 | 17 |
| Mooney Scorch, MS@121° C. | | | | | |
| Initial Viscosity (MU) | 42.34 | 41.97 | 42.13 | 42.94 | 43.37 |
| Minimum Viscosity (MU) | 29.8 | 29.12 | 28.93 | 31.15 | 31.25 |
| Final Viscosity (MU) | 44.82 | 44.15 | 43.94 | 46.17 | 46.27 |
| Mooney Scorch, MS@121° C. Aged 14 days at 40° C./95% relative humidity | | | | | |
| Initial Viscosity (MU) | 145.32 | 69.45 | 79.18 | 89.42 | 76.9 |
| Minimum Viscosity (MU) | 70.78 | 38.35 | 43.99 | 54.65 | 46.84 |
| Final Viscosity (MU) | 86.07 | 48.24 | 56.69 | 62.91 | 52.8 |
| Change Initial Viscosity (MU) | 102.98 | 27.48 | 37.05 | 46.48 | 33.53 |
| Change Minimum Viscosity (MU) | 40.98 | 9.23 | 15.06 | 23.5 | 15.59 |
| Oscillating Disk Rheometer - 60 minutes @ 160° C. | | | | | |
| Minimum Torque (ML) (dNm) | 2.02 | 1.98 | 2.14 | 1.98 | 2.06 |
| Maximum Torque (MH) (dNm) | 20.28 | 19.13 | 22.79 | 19.43 | 17.49 |
| Scorch time (ts2) (minutes) | 1.82 | 1.85 | 1.45 | 1.27 | 1.64 |
| Cure time (tc90) (minutes) | 6.6 | 27.96 | 27.42 | 24.08 | 25.84 |
| Physical Properties @ RT - Cure t95 + 5.0 Minutes - 160° C. | | | | | |
| Hardness - Shore A | 76 | 72 | 73 | 72 | 74 |
| Tensile Break (MPa) | 11.25 | 12.15 | 12.52 | 12.87 | 11.52 |
| Elongation Break (%) | 341.9 | 407.8 | 405.4 | 418.8 | 435.9 |
| 200% Modulus (MPa) | 7.4 | 7.03 | 6.93 | 6.77 | 6.47 |

Apparent from Table 6, samples incorporating the derivatives of the invention as a curative exhibited significantly improved stability over the sample containing Echo A, which is considered the standard curative for halogenated polymers. For example, the comparative sample containing Echo A (sample 13) exhibited an increase in initial viscosity of 102.98 Mooney units (MU) after being stored for 14 days. To the contrary, the inventive samples (samples 14–17)

exhibited increases in initial viscosity of only 27.48, 37.05, 46.48 and 33.53, respectively. Similar improvements in the change of minimum viscosity were also exhibited.

EXAMPLE 12

A bis 1,3,4-thiadiazole reaction product was prepared in the following manner. 17.2 grams of piperazine was combined with 30.4 grams of CS2 in a solvent mixture of 70 grams water and 150 grams of isopropyl alcohol. The mixture was held for about 1 hour at 30° C. Subsequently, 60 grams of 2,5-dimercapto-1,3,4-thiadiazole was added to the mixture and then 38.9 grams of 35 wt. hydrogen peroxide were added. The mixture was reacted for about 3 hours at 42° C. to yield a solid end product.

EXAMPLE 13

A study was conducted to evaluate the derivative prepared in accordance with Example 12 with the derivative prepared in accordance with Example 2. The samples were prepared by compounding the components listed in Table 7.

TABLE 7

| Components | Sample | |
|---|---|---|
| (parts by weight) | 18 | 19 |
| Tyrin ® CM0136 | 100 | 100 |
| N774 | 50 | 50 |
| Maglite ® D | 5 | 5 |
| Sundex © 790 | 30 | 30 |
| Durax © | 1 | 1 |
| Example 12 | 2.5 | |
| Example 2 | | 5.0* |

*To provide an equivalent ratio of thiadiazole moiety.

The compositions were pressed cured at 171° C. for 30 minutes. The samples were evaluated for Torque and scorch time by ASTM D2084 and Mooney parameters by ASTM D 1646 using a small rotor (MS). The results are listed in Table 8 below.

TABLE 8

| | Sample | |
|---|---|---|
| | 18 | 19 |
| Mooney Scorch, MS @ 121° C. | | |
| Minimum Viscosity, t5 (minutes) | 39.9 | 40.6 |
| Scorch, t5 (minutes) | 28.0 | 8.0 |
| Oscillating Disk Rheometer @ 171° C. | | |
| MinimumTorque (inch-pounds) | 0.7 | 0.7 |
| Maximum Torque (inch-pounds) | 10.7 | 10.5 |
| Scorch time (ts2) | 8.7 | 1.6 |
| Cure time (tc90) (minutes) | 41.6 | 26.3 |

EXAMPLE 14

The combined effectiveness of the derivative prepared in accordance with Example 12 with the derivative prepared in accordance with Example 2 was evaluated. The sample was prepared by compounding the components listed in Table 9.

TABLE 9

| Components (parts by weight) | Sample 20 |
|---|---|
| Tyrin ® CM0136 | 100 |
| N774 | 50 |
| Maglite ® D | 5 |
| Sundex ® 790 | 30 |
| Durax © | 1 |
| Example 12 | 2.5 |
| Example 2 | 1.25 |

A portion of the unaged sample was vulcanized, while another portion was aged for 7 days at 37.8° C. at 100% relative humidity(RH). The vulcanizates were formed by press curing for 30 minutes at 171° C. Mooney parameters, Scorch time and Torque were evaluated as in Example 13. The results are listed in Table 10.

TABLE 10

| Sample | 15-Unaged | 15-Aged |
|---|---|---|
| Mooney Scorch, NIS @ 121° C. | | |
| Minimum Viscosity, t5 (minutes) | 40.2 | 46.7 |
| Scorch, t5 (minutes) | 14.5 | 16.7 |
| Oscillating Disk Rheometer @ 171° C. | | |
| MinimumTorque (inch-pounds) | 0.7 | 0.9 |
| Maximum Torque (inch-pounds) | 15.4 | 14.6 |
| Scorch time (ts2) | 2.9 | 3.5 |
| Cure time (tc90) (minutes) | 22.9 | 28.3 |

Although the invention has been illustrated by reference to specific embodiments, it will be apparent to those skilled in the art that various changes and modifications may be made which clearly fall within the scope of the invention, and are intended to be claimed.

We claim:

1. An additive which is a reaction product of a 1,3,4-thiadiazole of formula (I):

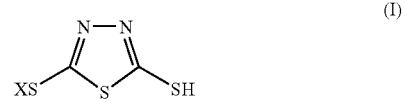

(I)

wherein X is hydrogen or a $C_1$–$C_{20}$ alkyl group and a dithiocarbamic acid of formula (IIa):

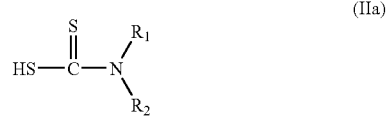

(IIa)

wherein $R_1$ and $R_2$ are independently a radical being either an alkyl, a cycloalkyl, an alkenyl, an aryl, an arylalkyl, or an alkylaryl, or $R_1$ and $R_2$ together form 3- to 8-membered heterocyclic ring structure which optionally contains an additional nitrogen or oxygen heteroatom and wherein the heterocyclic ring is optionally substituted with alkyl groups wherein the total number of carbon atoms from the heterocyclic ring alkyl groups is from 4 to 40,
wherein the reaction product is produced by reacting the dithiocarbmanic acid of formula (IIa) with the 1,3,4-thiadiazole of formula (I) and the oxidizing agent is then added; or
an isomer of said reaction product.

2. The additive of claim 1, wherein the 1,3,4-thiadiazole is 2,5-dimercapto-1,3,4-thiadiazole.

3. The additive of claim 1, wherein $R_1$ and $R_2$ are the same and are selected from the group consisting of ethyl, isopropryl and butyl.

4. The additive of claim 1, wherein $R_1$ and $R_2$ together form a piperazinyl ring.

5. The additive of claim 1, wherein the oxidizing agent is hydrogen peroxide.

6. The additive of claim 1, further comprising a diluent.

7. The additive of claim 1, wherein the dithiocarbamic acid of formula (IIa) is synthesized in situ by reacting carbon disulfide with the secondary amine of the formula $NHR_1R_2$, wherein $R_1$ and $R_2$ are independently a radical being either an alkyl, a cycloalkyl, an alkenyl, an aryl, an arylalkyl, or an alkylaryl, or $R_1$ and $R_2$ together form 3- to 8-membered heterocyclic ring structure which optionally contains an additional nitrogen or oxygen heteroatom.

8. A curable polymer composition comprising a major amount of at least one halogenated polymer and at least one additive of claim 1.

9. The curable polymer composition of claim 8, wherein the halogenated polymer is a chlorinated polymer.

10. The curable polymer composition of claim 9, wherein the chlorinated polymer is selected from the group consisting of homopolymers of epichlorohydrin, copolymers of epichlorohydrin and ethylene oxide or propylene oxide, polychloroprene, chlorinated polyolefins, chlorosulfonated polyolefin, polychloroalkylacrylates, chlorobutyl rubber and mixtures thereof.

11. The curable polymer composition of claim 10, wherein the chlorinated polyolefins is chloropolyethylene.

12. A method of preparing the additive of claim 1, which comprises reacting a dithiocarbamic acid of formula (IIa):

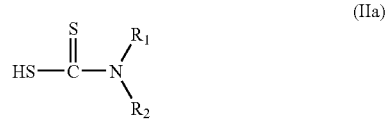

(IIa)

wherein $R_1$ and $R_2$ are independently a radical being either an alkyl, a cycloalkyl, an alkenyl, an aryl, an arylalkyl, or an alkylaryl, or $R_1$ and $R_2$ together form 3- to 8-membered heterocyclic ring structure which optionally contains an additional nitrogen heteroatom and wherein the heterocyclic ring is optionally substituted with alkyl groups wherein the total number of carbon atoms from the heterocyclic ring alkyl groups is from 4 to 40
with a 1,3,4-thiadiazole of formula (I):

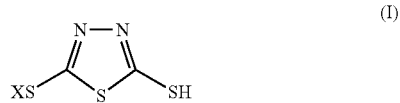

(I)

wherein X is hydrogen or a $C_1$–$C_{20}$ alkyl group,
in the presence of an oxidizing agent, to form a reaction product.

13. The process of claim 12, wherein the 1,3,4-thiadiazole is 2,5-dimercapto-1,3,4-thiadiazole.

14. The process of claim 12, wherein $R_1$ and $R_2$ are the same and are selected from the group consisting of ethyl, isopropryl and butyl.

15. The process of claim 12, wherein $R_1$ and $R_2$ together form a piperazinyl ring.

16. The process of claim 12, wherein the oxidizing agent is hydrogen peroxide.

17. The process of claim 12, further comprises adding a diluent to the reaction product.

18. The process of claim 12, wherein the dithiocarbamic acid of formula (II) is synthesized in situ by reacting carbon disulfide with the secondary amine of the formula $NHR_1R_2$, wherein $R_1$ and $R_2$ are independently a radical being either an alkyl, a cycloalkyl, an alkenyl, an aryl, an arylalkyl, or an alkylaryl, or $R_1$ and $R_2$ together form 3- to 8-membered heterocyclic ring structure which optionally contains an additional nitrogen or oxygen heteroatom.

19. An additive which is a reaction product of a 1,3,4-thiadiazole of formula (I):

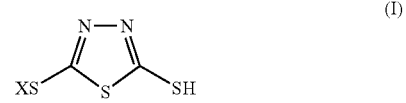

(I)

wherein X is hydrogen or a $C_1$–$C_{20}$ alkyl group and an amine of formula (IIb):

(IIb)

wherein $R_1$ and $R_2$ are independently a radical being either an alkyl, a cycloalkyl, an alkenyl, an aryl, an arylalkyl, or an alkylaryl, or $R_1$ and $R_2$ together form 3- to 8-membered heterocyclic ring structure which optionally contains an additional nitrogen or oxygen heteroatom and wherein the heterocyclic ring is optionally substituted with alkyl groups wherein the total number of carbon atoms from the heterocyclic ring alkyl groups is from 4 to 40,
wherein the reaction product is produced by reacting the amine of formula (IIb) with the 1,3,4-thiadiazole of formula (I), and the oxidizing agent is then added; or an isomer of said reaction product.

20. The additive of claim 19, wherein the 1,3,4-thiadiazole is 2,5-dimercapto-1,3,4-thiadiazole.

21. The additive of claim 19, wherein R1 and R2 are the same and are selected from the group consisting of ethyl, isopropyl, and butyl.

22. The additive of claim 19, wherein R1 and R2 together form a piperazinyl ring.

23. The additive of claim 19, wherein the oxidizing agent is hydrogen peroxide.

24. The additive of claim 19, further comprising a diluent.

25. The additive of claim 19, wherein R1 and R2 in the amine of formula NHR1 R2 are independently a radical being either an alkyl, a cycloalkyl, an alkenyl, an aryl, an arylalkyl, or an alkylaryl, or $R_1$ and $R_2$ together form 3- to 8-membered heterocyclic ring structure which optionally contains an additional nitrogen or oxygen heteroatom and wherein the heterocyclic ring is optionally substituted with alkyl groups wherein the total number of carbon atoms from the heterocyclic ring alkyl groups is from 4 to 40.

26. A curable polymer composition comprising a major amount of at least one halogenated polymer and at least one additive of claim 19.

27. The curable polymer composition of claim 26, wherein the halogenated polymer is a chlorinated polymer.

28. The curable polymer composition of claim 27, wherein the chlorinated polymer is selected from the group consisting of homopolymers of epichlorohydrin, copolymers of epichlorohydrin and ethylene oxide or propylene oxide, polychloroprene, chlorinated polyolefins, chlorosulfonated polyolefin, polychloroalkylacrylates, chlorobutyl rubber and mixtures thereof.

29. The curable polymer composition of claim 28, wherein the chlorinated polyolefins is chloropolyethylene.

30. A method of preparing the additive of claim 19, which comprises of reacting an amine of formula (IIb):

(IIb)

wherein $R_1$ and $R_2$ are independently a radical being either an alkyl, a cycloalkyl, an alkenyl, an aryl, an arylalkyl, or an alkylaryl, or $R_1$ and $R_2$ together form 3- to 8-membered heterocyclic ring structure which optionally contains an additional nitrogen or oxygen heteroatom and wherein the heterocyclic ring is optionally substituted with alkyl groups wherein the total number of carbon atoms from the heterocyclic ring alkyl groups is from 4 to 40, with a 1,3,4-thiadiazole of formula (I):

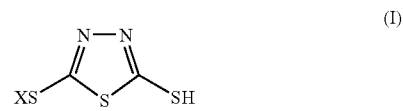

(I)

wherein X is hydrogen or a $C_1$–$C_{10}$ alkyl group, in the presence of an oxidizing agent to form a reaction product.

31. The process of claim 30, wherein the 1,3,4-thiadiazole is 2,5-dimercapto-1,3,4-thiadiazole.

32. The process of claim 30, wherein $R_1$ and $R_2$ are the same and are selected from the group consisting of ethyl, isopropryl and butyl.

33. The process of claim 30, wherein $R_1$ and $R_2$ together form a piperazinyl ring.

34. The process of claim 30, wherein the oxidizing agent is hydrogen peroxide.

35. The process of claim 30, further comprises adding a diluent to the reaction product.

36. The process of claim 30, wherein wherein $R_1$ and $R_2$ in the amine of formula (IIb) are independently a radical being either an alkyl, a cycloalkyl, an alkenyl, an aryl, an arylalkyl, or an alkylaryl, or $R_1$ and $R_2$ together form 3- to 8-membered heterocyclic ring structure which optionally contains an additional nitrogen or oxygen heteroatom and wherein the heterocyclic ring is optionally substituted with alkyl groups wherein the total number of carbon atoms from the heterocyclic ring alkyl groups is from 4 to 40.

* * * * *